United States Patent
Takezawa

(10) Patent No.: US 12,005,133 B2
(45) Date of Patent: *Jun. 11, 2024

(54) AQUEOUS COSMETIC

(71) Applicant: TOKIWA CORPORATION, Nakatsugawa (JP)

(72) Inventor: Shunpei Takezawa, Kawaguchi (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/191,874

(22) Filed: Mar. 29, 2023

(65) Prior Publication Data

US 2023/0233426 A1    Jul. 27, 2023

Related U.S. Application Data

(63) Continuation of application No. 16/846,408, filed on Apr. 13, 2020, now Pat. No. 11,642,292.

(30) Foreign Application Priority Data

Apr. 25, 2019 (JP) ................. 2019-084097

(51) Int. Cl.
*A61K 8/34* (2006.01)
*A61K 8/60* (2006.01)
*A61Q 1/10* (2006.01)

(52) U.S. Cl.
CPC .............. *A61K 8/345* (2013.01); *A61K 8/602* (2013.01); *A61Q 1/10* (2013.01); *A61K 2800/10* (2013.01); *A61K 2800/872* (2013.01)

(58) Field of Classification Search
None
See application file for complete search history.

(56) References Cited

U.S. PATENT DOCUMENTS

| | | | |
|---|---|---|---|
| 5,147,673 A * | 9/1992 | Schul .............. | C09B 61/00 426/540 |
| 6,214,322 B1 | 4/2001 | Castro et al. | |
| 6,641,823 B2 | 11/2003 | Piot et al. | |
| 9,877,565 B2 | 1/2018 | Sasaki | |
| 2002/0102283 A1 | 8/2002 | Piot et al. | |
| 2008/0102047 A1* | 5/2008 | Appel ............. | A61Q 1/10 424/70.6 |
| 2008/0131381 A1* | 6/2008 | Chaudhuri ........ | A61K 8/37 424/59 |
| 2010/0209371 A1 | 8/2010 | Casado-Chaudanson et al. | |
| 2011/0142891 A1* | 6/2011 | Pschirer .......... | A61K 8/342 424/401 |
| 2011/0177144 A1 | 7/2011 | Tashiro et al. | |
| 2012/0315230 A1 | 12/2012 | Chodorowski-Kimmes et al. | |
| 2013/0336903 A1* | 12/2013 | Fernandez Prieto .......... | A61K 8/4926 424/59 |
| 2015/0238405 A1 | 8/2015 | Wu | |
| 2018/0263870 A1* | 9/2018 | Foxcroft .......... | A61Q 17/04 |

FOREIGN PATENT DOCUMENTS

| | | |
|---|---|---|
| CN | 106810901 | 6/2017 |
| EP | 2196184 | 6/2010 |
| JP | 2000-034204 | 2/2000 |
| JP | 2008-013487 | 1/2008 |
| JP | 2010-180175 | 8/2010 |
| JP | 2010-534642 | 11/2010 |
| JP | 2016-087094 | 5/2016 |
| JP | 2017-078041 | 4/2017 |
| JP | 2017-114803 | 6/2017 |
| JP | 2019-011275 | 1/2019 |
| KR | 20090010768 | 1/2009 |
| TW | 200420678 | 10/2004 |
| WO | 2009/016323 | 2/2009 |

OTHER PUBLICATIONS

Zygmunt Marczenko et al., "Carminic Acid", Science Direct, 2000.
"1,3-Dihydroxyacetone dimer, Thermo Scientific®", Retrieved Nov. 19, 2022.
"Synperonic PE/L44", SpecialChem, Retrieved Nov. 19, 2022.

* cited by examiner

*Primary Examiner* — Danah Al-Awadi
(74) *Attorney, Agent, or Firm* — SOEI PATENT & LAW FIRM

(57) ABSTRACT

An aqueous cosmetic includes water, a polyhydric alcohol and carminic acid. A content of the carminic acid is greater than or equal to 0.2 mass % and less than 2 mass % based on a total amount of the aqueous cosmetic.

18 Claims, 1 Drawing Sheet

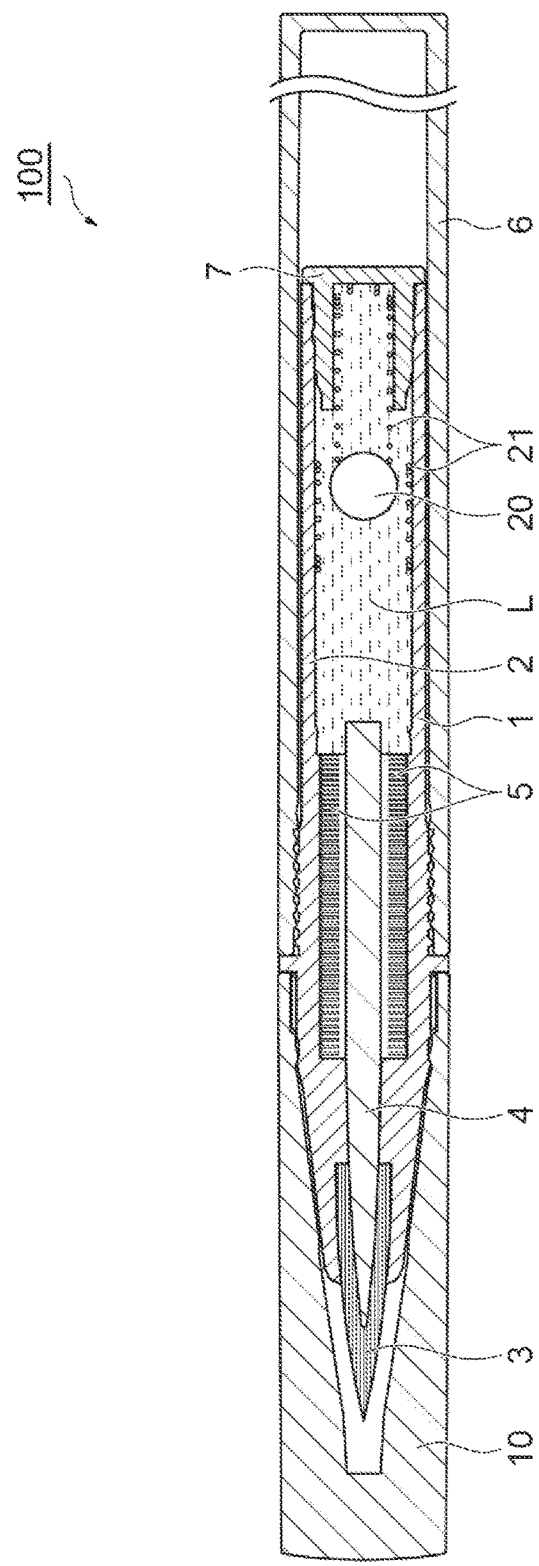

AQUEOUS COSMETIC

CROSS-REFERENCE TO RELATED APPLICATIONS

This application is a continuation of U.S. patent application Ser. No. 16/846,408, filed on Apr. 13, 2020 which is based upon and claims the benefit of priority from Japanese Patent Application No. 2019-084097, filed on Apr. 25, 2019, the entire contents of which are incorporated herein by reference.

TECHNICAL FIELD

The present application relates to an aqueous cosmetic.

BACKGROUND

Coloring materials are indispensable components for makeup cosmetic products. Organic synthetic pigments, which are inexpensive and stable and which have high color values, are mainly used in cosmetics containing coloring materials (for example, Japanese Unexamined Patent Publication No. 2010-180175). However, synthetic coloring materials for use are limited, depending on which part of the face a cosmetic is applied, and are restricted in certain countries or regions. Additionally, a liquid cosmetic container is described in Japanese Unexamined Patent Publication No. 2016-87094, and Japanese Unexamined Patent Publication No. 2008-13487 describes a cosmetic product containing a trace amount of carminic acid.

SUMMARY

Carminic acid, a natural coloring material, is a main coloring component of cochineal extracts. Carminic acid releases a hydrogen atom of a chromophore as the pH of an aqueous solution containing carminic acid shifts to an alkaline side to cause conjugation, and changes its color from orange to red. In addition, carminic acid is an unstable coloring matter which easily causes an oxidation reaction under the influence of light and heat which tends to discolor over time.

In known cosmetics containing a trace amount of carminic acid, the trace amount of carminic acid has been formulated in the cosmetic for the purpose of coloring the cosmetic itself and not for coloring a body part such as a user's face.

The present inventors have newly focused on obtaining a cosmetic containing a high concentration of carminic acid. However, they have found that a cosmetic containing a high concentration of carminic acid tends to cause the deposition of carminic acid and discoloration, and does not maintain a dissolved state of the carminic acid in the cosmetic for a long period of time.

Disclosed herein is an aqueous cosmetic that is configured to maintain a high concentration of the carminic acid in a stable condition for a long period of time.

In some examples, the aqueous cosmetic comprises water, a polyhydric alcohol and carminic acid, wherein a content of carminic acid is greater than or equal to 0.2 mass % and less than 2 mass % based on a total amount of the aqueous cosmetic.

The aqueous cosmetic may maintain the carminic acid in a stable condition for a long period of time even at a high concentration by virtue of a polyhydric alcohol contained therein. In addition, since the aqueous cosmetic employs carminic acid as a coloring material, which is a natural coloring matter, it may be suitably used for certain parts of the body or face, such as under and around a user's eyes, for which usable coloring materials are restricted in certain countries or regions.

In some examples, a content of the polyhydric alcohol in the aqueous cosmetic may be 0.5 to 70 mass % based on a total amount of the aqueous cosmetic. When a content of the polyhydric alcohol is within the above-described range, the stability of carminic acid can be further improved, and discoloration of carminic acid can be further suppressed.

In some examples, a content of water in the aqueous cosmetic may be 30 to 99.3 mass % based on a total amount of aqueous cosmetic. When a content of water is within the above-described range, deposition of carminic acid in the aqueous cosmetic can be further suppressed, and a dissolved state of carminic acid at a high concentration can be stably maintained for a long period of time.

In some examples, the polyhydric alcohol may have 2 to 6 hydroxy groups. This allows the aqueous cosmetic to be stably maintained for a longer period of time.

In some examples, the aqueous cosmetic may have a viscosity of 2 to 50 mPa·s as measured using a Brookfield viscometer at 25° C. When the viscosity is within this range, it is particularly suitable for a form of the aqueous cosmetic to be filled in a pen type container.

In some examples, the aqueous cosmetic may be applied under and around a user's eyes.

In some examples, a pen type aqueous cosmetic product comprises the aqueous cosmetic and a pen type container at least partially filled with the aqueous cosmetic.

BRIEF DESCRIPTION OF THE DRAWINGS

FIG. 1 is a schematic cross-sectional view showing an example pen type aqueous cosmetic product.

DETAILED DESCRIPTION

In the following description, with reference to the drawings, the same reference numbers are assigned to the same elements or to similar elements having the same function, and overlapping description is omitted.

Hereinafter, example embodiments will be described in detail.

An example aqueous cosmetic comprises a polyhydric alcohol and carminic acid, wherein a content of carminic acid is greater than or equal to 0.2 mass % and less than 2 mass % based on a total amount of the aqueous cosmetic.

In one or more embodiments, a content of carminic acid in the aqueous cosmetic may be greater than or equal to 0.2 mass %, greater than or equal to 0.3 mass %, or greater than or equal to 0.4 mass %, based on a total amount of the aqueous cosmetic. In one or more examples, color developability can be excellent and discoloration can be further suppressed by employing the cosmetic with a content of carminic acid in one of the increasingly higher ranges, such as "greater than or equal to 0.4 mass %". In one or more embodiments, a content of carminic acid may be less than 2.0 mass %, less than or equal to 1.9 mass %, less than or equal to 1.8 mass %, less than or equal to 1.7 mass %, or less than or equal to 1.5 mass %, based on a total amount of the aqueous cosmetic. When a content of carminic acid is less than 2.0 mass %, deposition of carminic acid can be suppressed. The amount of carminic acid can be quantitatively determined using high performance liquid chromatography.

The presence or absence of carminic acid in an aqueous cosmetic can be confirmed by $^1$H-NMR measurement.

Commercially available products, including Carmine Red K (Kiriya Chemical Co., Ltd.), Carmine Red MK-40 (Kiriya Chemical Co., Ltd.), CARMIN SOLUBLE W 3014 (Sensient Cosmetic Technologies), Kidrenin CA (Mitsubishi-Chemical Foods Corporation), Techno Color Red C2/CKD (Mitsubishi-Chemical Foods Corporation), Red 689 (TOYO ADL CORPORATION), and Creation Color RC (GLICO NUTRITION CO., LTD.), may be used as carminic acid.

In one or more embodiments, a content of water in the aqueous cosmetic may be greater than or equal to 28 mass %, greater than or equal to 30 mass %, greater than or equal to 35 mass %, greater than or equal to 40 mass %, greater than or equal to 45 mass %, greater than or equal to 50 mass %, greater than or equal to 55 mass %, greater than or equal to 60 mass %, greater than or equal to 65 mass %, greater than or equal to 70 mass %, greater than or equal to 75 mass %, or greater than or equal to 80 mass %, based on a total amount of the aqueous cosmetic. In some examples, deposition of carminic acid can be further suppressed by employing a content of water to be greater than or equal to 30 mass %.

In one or more embodiments, a content of water in the aqueous cosmetic may be less than 99.8 mass %, less than or equal to 99.5 mass %, less than or equal to 99.3 mass %, less than or equal to 99 mass %, less than or equal to 98 mass %, less than or equal to 97 mass %, less than or equal to 95 mass %, less than or equal to 93 mass %, or less than or equal to 90 mass %, based on a total amount of the aqueous cosmetic. In one or more embodiments, a content of water may be 30 to 99.3 mass % based on a total amount of the aqueous cosmetic. The water content in an aqueous cosmetic can be measured according to the Karl Fischer method.

In one or more embodiments, a proportion of carminic acid to water in the aqueous cosmetic may be less than or equal to 2 mass %. The deposition of carminic acid can be suppressed by employing a proportion of carminic acid to water to be less than or equal to 2 mass %. In one or more embodiments, a proportion of carminic acid to water may be less than or equal to 1.8 mass %, less than or equal to 1.6 mass %, less than or equal to 1.3 mass %, or less than or equal to 1.0 mass %. In one or more embodiments, a proportion of carminic acid to water may be greater than or equal to 0.1 mass %, greater than or equal to 0.2 mass %, greater than or equal to 0.3 mass %, or greater than or equal to 0.5 mass %.

A polyhydric alcohol refers to an alcohol having two or more alcoholic hydroxy groups in its molecule. A polyhydric alcohol may be an unsaturated polyhydric alcohol or a saturated polyhydric alcohol. The number of hydroxy groups in the polyhydric alcohol may be 2 to 6, 2 to 3, or 2. In one or more embodiments, the color stability of the aqueous cosmetic can be maintained for a longer period of time (for example, about half a year, one or more years) by employing the number of hydroxy groups in the polyhydric alcohol in one of the increasingly narrower ranges disclosed above, such as "2 to 3". From the same viewpoint, the number of carbon atoms in the polyhydric alcohol may be 2 to 8, 2 to 6, or 2 to 4. In addition, the molecular weight of the polyhydric alcohol may be 50 to 300, or 50 to 200.

Example of the polyhydric alcohol include 1,3-butylene glycol, propylene glycol, trimethylene glycol, 1,2-butylene glycol, tetramethylene glycol, 2,3-butylene glycol, pentaethylene glycol, 2-butene-1,4-diol, hexylene glycol, octylene glycol, glycerin, trimethylolpropane, pentaerythritol, xylitol, sorbitol, and mannitol. Butylene glycol may be employed from the viewpoints of appropriate molecular size and number of hydroxy groups.

In one or more embodiments, a content of the polyhydric alcohol may be less than or equal to 70 mass %, less than 70 mass %, less than or equal to 65 mass %, or less than or equal to 60 mass %, based on a total amount of the aqueous cosmetic. In some examples, carminic acid can be more stably contained in the aqueous cosmetic for a longer period of time by employing the content of the polyhydric alcohol in one of the increasingly lower ranges disclosed above, such as "less than or equal to 60 mass %". In one or more embodiments, a content of the polyhydric alcohol may be less than or equal to 55 mass %, less than or equal to 50 mass %, less than or equal to 45 mass %, less than or equal to 40 mass %, less than or equal to 35 mass %, less than or equal to 30 mass %, less than or equal to 25 mass %, less than or equal to 20 mass %, or less than or equal to 15 mass %, based on a total amount of the aqueous cosmetic.

In one or more embodiments, a content of the polyhydric alcohol may be greater than or equal to 0.5 mass % based on a total amount of the aqueous cosmetic. Carminic acid can be more stably contained in the aqueous cosmetic for a longer period of time by employing a content of the polyhydric alcohol to be greater than or equal to 0.5 mass %. In one or more examples, a content of the polyhydric alcohol may be greater than or equal to 0.8 mass %, greater than or equal to 1 mass %, greater than or equal to 3 mass %, greater than or equal to 5 mass %, greater than or equal to 8 mass %, or greater than or equal to 10 mass %, based on a total amount of the aqueous cosmetic. Accordingly, a content of the polyhydric alcohol may be 0.5 to 70 mass %, or 1 to 70 mass %, based on a total amount of the aqueous cosmetic.

In one or more embodiments, the aqueous cosmetic may be a non-emulsified type of cosmetic.

In one or more embodiments, the aqueous cosmetic may further comprise a small amount of an oil. For example, a content of the oil may be 0 to 10 mass %, 0 to 8 mass %, or 0 to 5 mass %, based on a total amount of the aqueous cosmetic.

In one or more embodiments, the aqueous cosmetic may further comprise a monohydric alcohol. In a case where the aqueous cosmetic comprises a monohydric alcohol, a content of the monohydric alcohol may be less than or equal to 30 mass %, less than or equal to 25 mass %, less than or equal to 20 mass %, less than or equal to 15 mass %, less than or equal to 10 mass %, less than or equal to 7 mass %, or less than or equal to 5 mass %, based on a total amount of the aqueous cosmetic. A content of the monohydric alcohol may be greater than or equal to 0.1 mass %, greater than or equal to 0.5 mass %, greater than or equal to 0.8 mass %, or greater than or equal to 1 mass %, based on a total amount of the aqueous cosmetic. Examples of the monohydric alcohol include ethanol, isopropyl alcohol, propanol, benzyl alcohol, and phenylpropanol.

In one or more embodiments, the aqueous cosmetic may further comprise a chelating agent. In other embodiments, the aqueous cosmetic may not contain a chelating agent. Even if the aqueous cosmetic does not contain any chelating agent, carminic acid can be stably maintained in the aqueous cosmetic for a long period of time according to the example compositions disclosed herein.

In one or more embodiments, the pH of the aqueous cosmetic may be 3 to 9, 4 to 9, 6 to 8.7, or 6.5 to 8.5. The color tone of carminic acid may be adjusted by controlling the pH. The pH can be adjusted with a pH adjuster.

In one or more embodiments, the aqueous cosmetic may further comprise a coloring agent in addition to carminic acid. Any dyes, coloring matters, pigment, or the like which are formulated with general cosmetics may be used as coloring agents. Examples of the dye include Red No. 227, Blue No. 1, Yellow No. 4, and Yellow No. 5. Examples of the coloring matter include natural coloring matters such as safflower. Examples of the pigment include inorganic coloring pigments, organic coloring pigments, and pearl pigments. Examples of the inorganic coloring pigment include carbon black, black iron oxide, red oxide, yellow iron oxide, cobalt oxide, chromium oxide, ultramarine blue, iron blue, titanium oxide, and zinc oxide. Examples of the organic coloring pigment include Red No. 228, Red No. 226, Blue No. 404, Red No. 202, Yellow No. 4 aluminum lake, and aluminum carminate lake. Examples of the pearl pigment include mica titanium, fish scale foil, and bismuth oxychloride.

In one or more embodiments, the aqueous cosmetic may further comprise an extender pigment. Examples of the extender pigment include silica, glass powder, silicic anhydride, aluminum silicate, magnesium silicate, aluminum-magnesium silicate, mica, synthetic mica, synthetic sericite, sericite, talc, kaolin, silicon carbide, barium sulfate, and resin particles such as PMMA (polymethyl methacrylate).

In one or more embodiments, the aqueous cosmetic may further comprise a thickener. In a case where a thickener is used, a moderate viscosity can be given to the aqueous cosmetic. Examples of the thickener for use include a polysaccharide-based thickener, a cellulose-based thickener, an alginic acid-based thickener, a vinyl-based thickener, an acrylic acid-based thickener, and an acrylic acid amide-based thickener.

Examples of the cellulose-based thickener include methyl cellulose, ethyl cellulose, carboxymethyl cellulose, hydroxyethyl cellulose, hydroxypropyl cellulose, and hydroxypropyl methyl cellulose. Examples of the alginic acid-based thickener include sodium alginate and propylene glycol alginate. Examples of the other polysaccharide-based thickener include sodium chondroitin sulfate, pectin, guar gum, xanthan gum, carrageenan, gellan gum, gum arabic, and sodium hyaluronate.

Examples of the vinyl-based thickener include polyvinyl alcohol (PVA), polyvinyl pyrrolidone (PVP), a vinyl pyrrolidone/vinyl acetate copolymer (VP/VA copolymer), a carboxyvinyl polymer, an alkylated carboxyvinyl polymer, and sodium polyacrylate. Examples of the acrylic acid-based thickener include an acrylic acid-alkyl methacrylate copolymer and an acrylic acid-alkyl acrylate copolymer. Examples of the acrylic acid amide-based thickener include a (hydroxyethyl acrylate/sodium acryloyldimethyltaurine) copolymer, a (sodium acrylate/sodium acryloyldimethyltaurine) copolymer, an (acryloyldimethyltaurine ammonium/VP) copolymer, and an (ammonium acryloyldimethyltaurate/beheneth-25 methacrylate) crosspolymer.

In one or more embodiments, the aqueous cosmetic may further comprise a dispersing agent. In some embodiments, the dispersion stability of a coloring agent other than carminic acid, particularly pigments, may be enhanced by employing the dispersing agent. For example, surfactants such as a hydrophilic nonionic surfactant, an anionic surfactant, a cationic surfactant, and an amphoteric surfactant may be used as dispersing agents.

Examples of the hydrophilic nonionic surfactant include polyoxyalkylene alkyl ethers, glycerin alkyl ethers, glycerin fatty acid esters, polyglycerin fatty acid esters, sorbitan fatty acid esters, and alkylene glycol adducts thereof, polyalkylene glycol fatty acid esters, polyglycerin-modified silicones, and polyether-modified silicones. Examples of the anionic surfactant include alkyl phosphates, polyoxyalkylene alkyl ether phosphates, sulfonates, alkyl sulfates, and polyaspartates. Examples of the cationic surfactant include alkylamine salts and alkyltrimethylammonium salts. Examples of the amphoteric surfactant include lecithin, carbobetaine-type amphoteric surfactants, sulfobetaine-type amphoteric surfactants, and amino acid-type amphoteric surfactants. The dispersing agent may be used alone, or two or more thereof may be used in combination. In one or more embodiments, a nonionic surfactant and/or an anionic surfactant may be used as dispersing agents.

In a case where the aqueous cosmetic comprises a dispersing agent, a content of the dispersing agent may be 0.005 to 2 mass %, 0.008 to 1.5 mass %, or 0.008 to 1 mass % based on a total amount of the aqueous cosmetic.

In one of more embodiments, the aqueous cosmetic may further comprise, for example, a preservative, a film-forming agent, a moisturizing agent, an ultraviolet absorbing agent, an ultraviolet scattering agent, an antioxidant, and a fragrance, in addition to the components described above. A content of the preservative may be, for example, 0 to 1 mass % based on a total amount of the aqueous cosmetic. A content of the film-forming agent may be, for example, 0 to 15 mass % or 1 to 10 mass % based on a total amount of the aqueous cosmetic.

In one or more embodiments, the aqueous cosmetic may have a viscosity of 1 to 2,000 mPa·s or 2 to 1,500 mPa·s at 25° C. When the aqueous cosmetic is filled in a pen type container to be described below, the viscosity of the aqueous cosmetic may be 2 to 50 mPa-s, 3 to 30 mPa·s, or 4 to 20 mPa·s. In some embodiments of the aqueous cosmetics filled in a pen type container, the dischargeability and fluidity of the aqueous cosmetics may be improved by employing the viscosity in one of the increasingly narrower ranges disclosed above, such as "4 to 20 mPa·s".

The above-described viscosity refers to a measured value of a sample at 25° C. using a Brookfield viscometer under the following conditions.

5 to 50 mPa·s: BL adapter with a rotational speed of 12 rpm 50 to 500 mPa·s: Rotor No. 1 with a rotational speed of 12 rpm 250 to 2,500 mPa·s: Rotor No. 2 with a rotational speed of 12 rpm 1,000 to 10,000 mPa-s: Rotor No. 3 with a rotational speed of 12 rpm 5,000 to 50,000 mPa·s: Rotor No. 4 with a rotational speed of 12 rpm The aqueous cosmetic may be suitable for makeup, and may be, for example, an eyebrow cosmetic, an eyeliner, an eye shadow, a lipstick, a lip liner, or a blusher. In many cases, use of carminic acid is approved even in countries or regions in which restrictions on coloring materials that can be used in cosmetics for under and around the eyes are severe. Therefore, the aqueous cosmetic comprising carminic acid may be suitably used as a cosmetic for under and around the eyes, such as an eyebrow cosmetic, an eyeliner, or an eye shadow.

In one or more embodiments, the aqueous cosmetic may be used as a cosmetic product. Examples of the cosmetic product include a pen type aqueous cosmetic product obtained by filling a pen type container with the aqueous cosmetic, and a bottle-type aqueous cosmetic product obtained by filling a bottle-type container with the aqueous cosmetic. Examples of the pen type aqueous cosmetic product include a mechanical type and an automatic pen type. The mechanical pen type aqueous cosmetic product may comprise a cosmetic storing part, such as a fiber bundle impregnated with a cosmetic or a part filled with a cosmetic, and an applicator comprising a brush or felt tip joined thereto. In the mechanical type product, the cosmetic is forcedly discharged by applying a force on the storing part by dialing or clicking. In the automatic pen type product, the cosmetic is discharged through the action of its surface tension and capillary phenomenon.

In some embodiments, the aqueous cosmetic may be utilized in an automatic pen type from the viewpoints of convenience in use and portability. The automatic pen type product may employ an automatic pen type container configured to hold an aqueous cosmetic product.

FIG. 1 is a schematic cross-sectional view showing an example pen type aqueous cosmetic product 100. The overall shape of the pen type aqueous cosmetic product 100 resembles a writing tool in an elongated narrow round-bar form. In some examples, the pen type aqueous cosmetic product 100 comprises a cylindrical container body 1, a storing part 2 disposed in the container body 1 so as to accommodate an aqueous cosmetic L, and a brush 3 installed at a tip of the container body 1 for the application of the aqueous cosmetic L in the storing part 2. Additionally, the pen type aqueous cosmetic product 100 may comprise a shaft-like relay wick 4 disposed in the container body 1 for connecting the inner part of the storing part 2 to the brush 3, and a bellows component 5 in a substantially cylindrical shape installed around the relay wick 4. In some examples, a grip tube 6 in a bottomed-cylindrical shape is screwed to the container body 1 for detachable installation so that a user holding the container body 1 can easily apply the cosmetic. The shape of the container body 1 may be a cylindrical or rectangular tube, or some other shape.

The container body 1 is formed of, for example, polypropylene (PP), and is configured to be a tapered cylindrical shape having a flange. A rear end face of the flange part disposed on an outer peripheral surface of the container body 1 abuts on a front end face of the gripping cylinder 6 screwed into the container body 1. A front end face of the flange part abuts on an open end face of a cap 10 installed on the container body 1. An opening at a rear end of the container body 1 is closed with a bottomed cylindrical tale plug 7 inserted therein.

The bellows component 5 is configured to control the flow rate of the aqueous cosmetic L and has grooves (bellows) containing the aqueous cosmetic L. A cylindrical rear end part of the bellows component 5 fits in a recess of an inner peripheral face of the container body 1 so that the bellows component 5 is installed within the container body 1. The storing part 2 is formed between the rear end part of the bellows component 5 in the container body 1 and the tail plug 7, and the aqueous cosmetic L is accommodated in this storing part 2.

The relay wick 4 is, for example, formed of an acrylic resin and extends in the axial direction so as to pass through the tube hole of the bellows component 5. A tip of the relay wick 4 fits into a tip of the bellows component 5 so that the relay wick 4 is installed within the bellows component 5. The relay wick 4 connects the inner part of the storing part 2 to the brush 3, while its rear end part enters into the inner part of the storing part 2 and its front end part enters into the brush 3. The relay wick 4 allows the aqueous cosmetic L to be sucked from the storing part 2 by capillary phenomenon and to be supplied to the brush 3.

The brush serves as an applicator in the pen type aqueous cosmetic product 100 shown in FIG. 1, but it may be replaced by a tip such as a felt tip, a urethane tip, a nylon tip, a polyester tip, or an olefin tip.

The bottomed cylindrical cap 10 is detachably installed at the tip of the container body 1 by fitting to protect the brush 3.

In the pen type aqueous cosmetic product 100, a stirring element 20 that can move in the axial direction and a coil spring 21 that can extend and contract in the axial direction are accommodated in the storing part 2 together with the aqueous cosmetic L. In FIG. 1, the stirring element 20 is depicted as a sphere; however, the element may be a polyhedron, a cone, or other shape depending on the particular application.

The coil spring 21 is an integrally formed spring in which a plurality of spring portions having different diameters (e.g., two spring portions having different diameters as illustrated in FIG. 1) are integrally connected to in the axial direction, and the coil spring may be formed of SUS (Steel Use Stainless) for example. The coil spring 21 includes a small-diameter spring portion having a smaller diameter than that of the stirring element 20 in its rear half part and a large-diameter spring portion having a larger diameter than that of the stirring element 20 continuously, the latter of which spring portions is adjacent to the forward axial direction of the small-diameter spring portion adjacent in the axial direction.

The stirring element 20 is movable in the axial direction within the large-diameter spring portion constituting the coil spring 21. Thus, when a user shakes the pen type aqueous cosmetic product 100, the stirring element 20 moves in the axial direction, and the aqueous cosmetic L can be stirred by the movement of the stirring element 20.

In the pen type aqueous cosmetic product 100 configured in this manner, the aqueous cosmetic L in the storing part 2 flows toward the brush 3 at a front side of the container through the relay wick 4 and is provided to a user for application with the brush 3. The pen type aqueous cosmetic product 100 includes the stirring element 20 and the coil spring 21, thereby allowing the aqueous cosmetic L to efficiently flow toward the brush 3. The configuration of the pen type aqueous cosmetic product may be changed such that it neither includes the stirring element 20 nor the coil spring 21.

Example automatic pen type containers that may utilize the aqueous cosmetic have been described above by referring to the pen type aqueous cosmetic container 100 having a so-called direct liquid type structure. However, other types of structures may be used. For example, a container having a so-called cotton wadding-type structure may be used, which omits the bellows member 5, the stirring element 20, and the coil spring 21 in the pen type aqueous cosmetic product 100. The container may have a storing part accommodating a cotton wadding member impregnated with the aqueous cosmetic L and the wadding member may be configured to suck the aqueous cosmetic L from the storing part in order to supply the aqueous cosmetic to the brush 3 through a rear end part of the relay wick 4 entering into an inner part of the wadding-type structure.

Hereinafter, details of additional example embodiments will be described with reference to comparative examples.

Test Example 1

Components shown in Tables 1 and 2 were mixed at proportions (mass %) shown in the tables to prepare aqueous cosmetics for bottle-type cosmetic containers. The following components were used as the components shown in the tables. The proportion of water in the tables varies depending on the amount of pH adjusting agent used. Therefore, the proportion of water is expressed as a range and at least falls within each range shown in the tables.

Carminic acid: CARMIN SOLUBLE W3014 (manufactured by Sensient Cosmetic Technologies). The proportions shown in the tables are net weights of carminic acid.

Film-forming acrylic acid polymer emulsion: Daitosol 5000SJ (manufactured by Daito Kasei Kogyo Co., Ltd.) The proportions shown in the tables are the values as converted into solid contents.

Film-forming acrylic acid polymer: Plus Size L-9540U (manufactured by Goo Chemical Co., Ltd.) The proportions shown in the tables are the values as converted into solid contents.

Acrylic Acid Amide-Based Thickener: SEPINOV EMT 10 (Manufactured by SEPPIC)

The viscosity, deposition, and color stability of each of the obtained aqueous cosmetics were evaluated according to the following methods. In addition, the proportion (mass %) of carminic acid to water in each aqueous cosmetic was calculated. The proportion of carminic acid to water is also expressed as a range similarly to the proportion of water, and at least falls within each range shown in the tables.

Viscosity

The viscosity of an aqueous cosmetic at 25° C. was measured using a Brookfield viscometer under the following conditions.

5 to 50 mPa·s: BL adapter with a rotational speed of 12 rpm
50 to 500 mPa·s: Rotor No. 1 with a rotational speed of 12 rpm
250 to 2,500 mPa·s: Rotor No. 2 with a rotational speed of 12 rpm
1,000 to 10,000 mPa·s: Rotor No. 3 with a rotational speed of 12 rpm
5,000 to 50,000 mPa·s: Rotor No. 4 with a rotational speed of 12 rpm Deposition Evaluation (Screw Tube)

Immediately after the preparation of the aqueous cosmetics, fifty grams of each aqueous cosmetic was placed in a screw tube and was stored at 25° C. or 50° ° C. for one month in a state where the screw tube was closed with a lid. Samples in which no deposition was visually observed after storage for one month at both 25° C. and 50° C. were scored "A", and samples in which depositions were observed at 25° C. within one week were scored "C".

Color Stability (Screw Tube)

Fifty grams of each aqueous cosmetic was placed in a screw tube immediately after the preparation of the aqueous cosmetic. A cotton swab was immersed in the aqueous cosmetic in the screw tube, and a line was drawn on paper with the cotton swab. The color of the drawn line was visually observed. Then, the aqueous cosmetic was stored at 25° C. or 50° C. for one month in a state where the screw tube was closed with a lid. Similarly, a cotton swab was immersed in each aqueous cosmetic and a line was drawn on paper after the storage for one month. The color of the drawn line was visually observed and compared with the color of the drawn line immediately after the preparation. Samples in which no discoloration was observed at both 25° C. and 50° C. after the storage were scored "A"; samples in which discoloration was observed at a storage temperature of 50° C. while no discoloration was observed at a storage temperature of 25° C. were scored "B"; and samples in which discoloration was observed at both 25° C. and 50° C. were scored "C".

TABLE 1

| | Example 1 | Example 2 | Example 3 | Example 4 | Example 5 | Example 6 |
|---|---|---|---|---|---|---|
| Carminic acid | 0.5 | 0.5 | 0.5 | 0.5 | 0.5 | 0.5 |
| Butylene glycol | 10 | 1 | 30 | 50 | 60 | 0.05 |
| pH Adjuster | | | Appropriately | | | |
| Water (balance) | 84.36 to 89.36 | 93.36 to 98.36 | 64.36 to 69.36 | 44.36 to 49.36 | 34.36 to 39.36 | 94.31 to 99.31 |
| Proportion (mass %) of carminic acid to water | 0.560 to 0.593 | 0.508 to 0.536 | 0.721 to 0.777 | 1.013 to 1.127 | 1.270 to 1.455 | 0.503 to 0.530 |
| pH | 8.5 | 7.5 | 6.0 | 8.0 | 6.5 | 6.5 |
| Deposition (screw tube) | A | A | A | A | A | A |
| Color stability (screw tube) | A | A | A | A | A | B |

TABLE 2

| | Example 7 | Example 8 | Example 9 | Example 10 | Example 11 | Comp. Example 1 | Comp. Example 2 |
|---|---|---|---|---|---|---|---|
| Carminic acid | 0.5 | 0.5 | 0.5 | 0.5 | 1.4 | 2.0 | 0.05 |
| Butylene glycol | — | — | — | — | 10 | 10 | 10 |
| Pentylene glycol | 10 | — | — | — | — | — | — |
| Dipropylene glycol | — | 10 | — | — | — | — | — |
| Sorbitol | — | — | 10 | — | — | — | — |
| Glycerin | — | — | — | 10 | — | — | — |
| pH Adjuster | | | | Appropriately | | | |
| Water (balance) | 84.36 to 89.36 | 84.36 to 89.36 | 84.36 to 89.36 | 84.36 to 89.36 | 83.21 to 88.21 | 82.44 to 87.44 | 84.94 to 89.94 |
| Proportion (mass %) of carminic acid to water | 0.560 to 0.593 | 0.560 to 0.593 | 0.560 to 0.593 | 0.560 to 0.593 | 1.587 to 1.683 | 2.287 to 2.426 | 0.056 to 0.059 |
| pH | 6.5 | 6.5 | 6.5 | 6.5 | 6.5 | 6.5 | 6.5 |
| Deposition (screw tube) | A | A | A | A | A | C | A |
| Color stability (screw tube) | A | A | A | A | A | — | C |

The aqueous cosmetics stored in the screw tubes in the examples could stably contain carminic acid even after long-term storage. Deposition was observed in the aqueous cosmetic of Comparative Example 1 at a storage temperature of 25° C. within one week. Since deposition occurred in the aqueous cosmetic of Comparative Example 1, the color stability of dissolved carminic acid could not be evaluated. Since the amount of carminic acid in the aqueous cosmetic of Comparative Example 2 was too small, a sufficient color value could not be obtained from the beginning of preparation, and discoloration during storage was observed.

Test Example 2

Aqueous cosmetics having formulations shown in Tables 3, 4 and 5 were prepared as eyebrow cosmetics to be filled in automatic pens. Evaluation was performed on filled automatic pen products in addition to the above-described evaluation performed on the screw tubed products. Specifically, for deposition evaluation, an automatic pen type container was filled with an aqueous cosmetic and stored at 25° C. or 50° C. for one month in a state where the pen type container was closed with a lid. Samples in which no deposition was observed in the applicators (brushes) of pen type containers at both 25° C. and 50° C. for one month were scored "A", and samples in which deposition was observed at 25° C. within one week were scored "C". For evaluation of color stability, a line was drawn on paper with a pen filled with an aqueous cosmetic, and the color of a drawn line after the storage of the aqueous cosmetic for one month was compared with the color of a drawn line immediately after the preparation of an aqueous cosmetics similarly to the cases of the screw tubes. Samples in which no discoloration was observed after storage of one month from immediately after the preparation at both 25° C. and 50° C. were scored "A"; samples in which discoloration was observed at a storage temperature of 50° C. while no discoloration was observed at a storage temperature of 25° C. were scored "B"; and samples in which discoloration was observed at both 25° C. and 50° C. were scored "C".

TABLE 3

|  | Example 12 | Example 13 | Example 14 | Example 15 | Example 16 |
|---|---|---|---|---|---|
| Butylene glycol | 10.0 | 10.0 | 10.0 | 10.0 | 10.0 |
| Ethanol | 1.0 | 1.0 | 1.0 | 5.0 | 1.0 |
| Carminic acid | 1.4 | 0.5 | 0.5 | 0.5 | 0.3 |
| Blue No. 1 | 0.08 | 0.03 | 0.03 | 0.03 | 0.02 |
| Yellow No. 4 | 0.2 | 0.1 | 0.1 | 0.1 | 0.1 |
| Xanthan gum | 0.02 | 0.05 | 0.04 | 0.05 | 0.04 |
| Polyvinyl pyrrolidone | — | — | — | — | — |
| Film-forming acrylic acid polymer emulsion | — | — | 6.0 | — | — |
| Film-forming acrylic acid polymer | — | — | — | 3.2 | — |
| Preservative | 0.8 | 0.8 | 0.8 | 0.8 | 0.8 |
| pH Adjuster | Appropriately | | | | |
| Water (balance) | 81.13 to 86.13 | 82.43 to 87.43 | 76.39 to 81.39 | 75.20 to 80.20 | 82.75 to 87.75 |
| Proportion (mass %) of carminic acid to water | 1.625 to 1.726 | 0.572 to 0.607 | 0.614 to 0.655 | 0.623 to 0.665 | 0.342 to 0.363 |
| pH | 7.5 | 7.5 | 7.5 | 7.5 | 7.5 |
| Viscosity | 5.00 | 12.00 | 9.00 | 15.50 | 9.00 |
| Deposition (screw tube) | A | A | A | A | A |
| Color stability (screw tube) | A | A | A | A | A |
| Deposition (pen applicator) | A | A | A | A | A |
| Color stability (drawn line) | A | A | A | A | A |

TABLE 4

|  | Example 17 | Example 18 | Example 19 | Example 20 |
|---|---|---|---|---|
| Butylene glycol | 30.0 | 35.0 | 1.0 | 10.0 |
| Ethanol | — | 25.0 | — | — |
| Carminic acid | 0.5 | 0.5 | 0.5 | 0.5 |
| Blue No. 1 | 0.03 | 0.03 | 0.03 | 0.03 |
| Yellow No. 4 | 0.3 | 0.1 | 0.1 | 0.1 |
| Xanthan gum | 0.03 | 0.04 | 0.04 | 0.04 |
| Polyvinyl pyrrolidone | — | — | — | 0.04 |
| Film-forming acrylic acid polymer emulsion | — | — | — | — |
| Film-forming acrylic acid polymer | — | — | — | — |
| Preservative | 0.8 | 0.8 | 0.8 | 0.8 |
| pH Adjuster | Appropriately | | | |
| Water (balance) | 63.25 to 68.25 | 33.46 to 38.46 | 92.46 to 97.46 | 83.39 to 88.39 |
| Proportion (mass %) of carminic acid to water | 0.733 to 0.791 | 1.300 to 1.494 | 0.513 to 0.541 | 0.566 to 0.600 |
| pH | 7.5 | 7.5 | 7.5 | 7.5 |
| Viscosity | 7.00 | 9.00 | 9.00 | 5.00 |
| Deposition (screw tube) | A | A | A | A |
| Color stability (screw tube) | A | A | A | A |
| Deposition (pen applicator) | A | A | A | A |
| Color stability (drawn line) | A | A | A | A |

TABLE 5

|  | Example 21 | Example 22 | Example 23 |
|---|---|---|---|
| Butylene glycol | 10.0 | 10.0 | 10.0 |
| Ethanol | 1.0 | 1.0 | 1.0 |
| Carminic acid | 0.5 | 0.5 | 0.5 |
| Blue No. 1 | 0.03 | 0.03 | 0.03 |
| Yellow No. 4 | 0.1 | 0.1 | 0.1 |
| Xanthan gum | 0.04 | 0.04 | 0.04 |
| Preservative | 0.8 | 0.8 | 0.8 |
| Film-forming acrylic acid polymer emulsion | 4.0 | 4.0 | 4.0 |
| Polyoxyethylene alkyl ether | 0.01 | 0.08 | 0.80 |
| Polyoxyethylene glycerin fatty acid ester | 0.01 | 0.05 | 0.40 |
| Carbon black | 0.03 | 0.20 | 2.00 |
| Iron oxide | 0.01 | 0.70 | 7.00 |
| pH Adjuster | Appropriately | | |
| Water (balance) | 78.36 to 83.36 | 77.38 to 82.38 | 68.21 to 73.21 |
| Proportion (mass %) of carminic acid to water | 0.600 to 0.638 | 0.607 to 0.646 | 0.683 to 0.733 |
| pH | 7.5 | 7.5 | 7.5 |
| Viscosity | 9.00 | 9.00 | 9.00 |
| Deposition (screw tube) | A | A | A |
| Color stability (screw tube) | A | A | A |
| Deposition (pen applicator) | A | A | A |
| Color stability (drawn line) | A | A | A |

Even when aqueous cosmetics were filled in an automatic pen, the aqueous cosmetics of the examples which contain a polyhydric alcohol and carminic acid and of which the concentrations of carminic acid were greater than or equal to 0.2 mass % and less than 2 mass % based on a total amount of the aqueous cosmetic could stably contain carminic acid for a long period of time.

Test Example 3

Hereinafter, examples of other aqueous cosmetics will be shown. Similarly to the above-described test examples, the pH, the viscosity, the deposition and color stability of screw tubed products or filled automatic pen products were evaluated.

Example 24

A blusher having the following formulation was prepared.
Butylene glycol 10.0 mass %
Carminic acid 1.0 mass %
Blue No. 1 0.01 mass %
Yellow No. 4 0.1 mass %
Acrylic acid amide-based thickener 1.7 mass %
Preservative 0.8 mass %
pH Adjuster Appropriately
Water (balance) 81.19 to 86.19 mass %
Proportion of carminic acid to water 1.160 to 1.232 mass %
pH 7.5
Viscosity 1,425 mPa·s
Deposition (screw tube) A
Color stability (screw tube) A Example 25

A cosmetic for lips having the following formulation was prepared.
Butylene glycol 10.0 mass %
Ethanol 1.0 mass %
Carminic acid 1.4 mass %
Carbomer 0.03 mass %
Film-forming acrylic acid polymer emulsion 5.0 mass %
Preservative 0.8 mass %
pH Adjuster Appropriately
Water (balance) 76.43 to 81.43 mass %
Proportion of carminic acid to water 1.719 to 1.832 mass %
pH 7.5
Viscosity 3.25 mPa·s
Deposition (screw tube) A
Color stability (screw tube) A Example 26

An eyeliner having the following formulation was prepared.
Butylene glycol 10.0 mass %
Carminic acid 0.6 mass %
Blue No. 1 0.075 mass %
Yellow No. 4 0.075 mass %
Film-forming acrylic acid polymer emulsion 10.0 mass %
Preservative 0.8 mass %
pH Adjuster Appropriately
Water (balance) 73.28 to 78.28 mass %
Proportion of carminic acid to water 0.766 to 0.819 mass %
pH 7.5
Viscosity 2.5 mPa·s
Deposition (screw tube) A
Color stability (screw tube) A
Deposition (pen applicator) A
Color stability (drawn line) A It is to be understood that not all aspects, advantages and features described herein may necessarily be achieved by, or included in, any one particular embodiment. Indeed, having described and illustrated various embodiments herein, it should be apparent that other embodiments may be modified in composition and detail. We claim all modifications and variations coming within the spirits and scope of the subject matter claimed herein.

What is claimed is:

1. An aqueous cosmetic consisting of:
   water;
   at least one polyhydric alcohol selected from the group consisting of 1,3-butylene glycol, propylene glycol, trimethylene glycol, 1,2-butylene glycol, tetramethylene glycol, 2,3-butylene glycol, pentamethylene glycol, 2-butene-1,4-diol, hexylene glycol, octylene glycol, glycerin, trimethylolpropane, pentaerythritol, xylitol, sorbitol, and mannitol;
   carminic acid dissolved in the aqueous cosmetic; and
   at least one agent selected from the group consisting of one or more pH adjusters, thickeners, dyes, pigments, monohydric alcohols, dispersing agents, preservatives, film-forming agents, moisturizing agents, ultraviolet scattering agents, antioxidants and fragrances,
   wherein the one or more dyes are Red No. 227, Blue No. 1, Yellow No. 4, Yellow No. 5 or a mixture thereof,
   wherein the one or more monohydric alcohols are ethanol, isopropyl alcohol, propanol, benzyl alcohol, phenylpropanol or a mixture thereof, and
   wherein a content of the carminic acid is greater than or equal to 0.2 mass % and less than 2 mass % based on a total amount of the aqueous cosmetic.

2. An aqueous cosmetic consisting of:
   water;
   at least one polyhydric alcohol selected from the group consisting of 1,3-butylene glycol, propylene glycol, trimethylene glycol, 1,2-butylene glycol, tetramethylene glycol, 2,3-butylene glycol, pentamethylene glycol, 2-butene-1,4-diol, hexylene glycol, octylene glycol, glycerin, trimethylolpropane, pentaerythritol, xylitol, sorbitol, and mannitol;
   carminic acid dissolved in the aqueous cosmetic; and
   at least one agent selected from the group consisting of one or more oils, chelating agents, pH adjusters, thickeners, dyes, pigments, monohydric alcohols, dispersing agents, preservatives, film-forming agents, moisturizing agents, ultraviolet scattering agents, antioxidants and fragrances,
   wherein the one or more dyes are Red No. 227, Blue No. 1, Yellow No. 4, Yellow No. 5 or a mixture thereof,
   wherein the one or more monohydric alcohols are ethanol, isopropyl alcohol, propanol, benzyl alcohol, phenylpropanol or a mixture thereof, and
   wherein a content of the carminic acid is greater than or equal to 0.2 mass % and less than 2 mass % based on a total amount of the aqueous cosmetic.

3. The aqueous cosmetic according to claim 2, wherein the one or more pigments are an inorganic coloring pigment, a pearl pigment, Red No. 228, Red No. 226, Blue No. 404, Red No. 202, Yellow No. 4 aluminum lake or a mixture thereof.

4. The aqueous cosmetic according to claim 2, wherein the at least one polyhydric alcohol is selected from the group consisting of 1,3-butylene glycol, propylene glycol, trimethylene glycol, 1,2-butylene glycol, tetramethylene glycol, 2,3-butylene glycol, pentamethylene glycol, 2-butene-1,4-diol, hexylene glycol, octylene glycol, trimethylolpropane, and pentaerythritol.

5. The aqueous cosmetic according to claim 2, wherein a content of the polyhydric alcohol is 0.5 to 70 mass % based on the total amount of the aqueous cosmetic.

6. The aqueous cosmetic according to claim 2, wherein a proportion of carminic acid to water in the aqueous cosmetic is greater than or equal to 0.3 mass % and less than or equal to 2 mass %.

7. The aqueous cosmetic according to claim 2, wherein the aqueous cosmetic has a viscosity of 2 to 50 mPa·s at 25° C. as measured using a Brookfield viscometer.

8. The aqueous cosmetic according to claim 2, wherein a pH of the aqueous cosmetic is 6 to 9.

9. The aqueous cosmetic according to claim 2, wherein the aqueous cosmetic is a non-emulsified cosmetic.

10. A pen-shaped aqueous cosmetic product comprising:
the aqueous cosmetic according to claim 2; and
a pen-shaped container at least partially filled with the aqueous cosmetic.

11. A pen-shaped aqueous cosmetic product comprising:
the aqueous cosmetic according to claim 1; and
a pen-shaped container at least partially filled with the aqueous cosmetic.

12. The aqueous cosmetic according to claim 1, wherein the one or more pigments are an inorganic coloring pigment, a pearl pigment, Red No. 228, Red No. 226, Blue No. 404, Red No. 202, Yellow No. 4 aluminum lake or a mixture thereof.

13. The aqueous cosmetic according to claim 1, wherein the at least one polyhydric alcohol is selected from the group consisting of 1,3-butylene glycol, propylene glycol, trimethylene glycol, 1,2-butylene glycol, tetramethylene glycol, 2,3-butylene glycol, pentamethylene glycol, 2-butene-1,4-diol, hexylene glycol, octylene glycol, trimethylolpropane, and pentaerythritol.

14. The aqueous cosmetic according to claim 1, wherein a content of the polyhydric alcohol is 0.5 to 70 mass % based on the total amount of the aqueous cosmetic.

15. The aqueous cosmetic according to claim 1, wherein a proportion of carminic acid to water in the aqueous cosmetic is greater than or equal to 0.3 mass % and less than or equal to 2 mass %.

16. The aqueous cosmetic according to claim 1, wherein the aqueous cosmetic has a viscosity of 2 to 50 mPa·s at 25° C. as measured using a Brookfield viscometer.

17. The aqueous cosmetic according to claim 1, wherein a pH of the aqueous cosmetic is 6 to 9.

18. The aqueous cosmetic according to claim 1, wherein the aqueous cosmetic is a non-emulsified cosmetic.

* * * * *